United States Patent [19]

Klein

[11] 4,318,694
[45] Mar. 9, 1982

[54] TOOTH-TO-TOOTH RETAINER WIRE INSTALLATION APPARATUS

[76] Inventor: Paul E. Klein, 601 First St., Lake Oswego, Oreg. 97034

[21] Appl. No.: 208,798

[22] Filed: Nov. 20, 1980

[51] Int. Cl.³ .............................................. A61C 7/00
[52] U.S. Cl. ........................................ 433/22; 433/18
[58] Field of Search ..................... 433/8, 18, 11, 22, 5, 433/6, 7; 24/150 B, 150 FP, 159, 236

[56] References Cited

U.S. PATENT DOCUMENTS

| Re. 29,686 | 7/1978 | Wallshain | 433/18 |
| 3,973,299 | 8/1976 | Keefe | 24/150 FP |
| 4,202,328 | 5/1980 | Sukkarie | 433/18 |

Primary Examiner—Robert Peshock
Attorney, Agent, or Firm—Kolisch, Hartwell & Dickinson

[57] ABSTRACT

An elasticized stabilizer for temporarily immobilizing a tooth-to-tooth retainer wire as commonly applied in orthodontia. The stabilizer comprises an elongated filament with modifications or enlargements on each end. When the filament is stretched and placed between two adjacent teeth, the retainer wire is urged toward the teeth and held in position during installation.

8 Claims, 6 Drawing Figures

TOOTH-TO-TOOTH RETAINER WIRE INSTALLATION APPARATUS

BACKGROUND AND SUMMARY OF THE INVENTION

This invention pertains to an elasticized stabilizer for temporarily immobilizing a tooth-to-tooth retainer wire as commonly applied in orthodontia. The stabilizer comprises an elongated filament one end of which is modified to engage the retainer wire and hold it close to or against one side of the teeth. The other end of the filament has an enlargement which applies a restraining force against the opposite side of the teeth. The stretched condition of the filament causes the retainer wire to be immobilized.

During conventional installation of a retainer wire the tooth surfaces are prepared and the wire is placed along the tooth arch. It is then held in place either manually, with ligature wire, or with sticky wax while a bonding agent is applied. The wire must be held for a period of time until the bonding agent sets.

There are several disadvantages to these methods. The manual method causes patient discomfort and proper positioning of the restainer wire is difficult to maintain due to the inherent motion that exists between patient and doctor. This method also requires the time and effort of the doctor when he or she could be more productively engaged in other activities. The use of ligature wire is time consuming and somewhat awkward. Sticky wax is easily applied but does not provide a positive force on the retainer wire toward the teeth.

It is an object of the present invention to provide a mechanical method of temporarily immobilizing a retainer wire during its installation which overcomes the above-described shortcomings of prior art retainer wire installation.

It is a further object of the present invention to provide a stabilizer which is easily installed, manipulated and removed.

Yet another object of the present invention is to provide a stabilizer which has general applicability so that it may be used in a variety of installation situations.

The three preferred embodiments of this invention generally comprise an elongated filament portion one end of which is modified for engaging a retainer wire and for urging it toward teeth. The other end of the filament portion takes the form of an enlargement incapable of passage between adjacent teeth. The retainer wire is immobilized by engaging it with the stabilizer and by then stretching the filament portion and sliding it between adjacent teeth with the enlargement on the opposite side of the teeth from the retainer wire.

One embodiment engages a wire with an eyelet which is joined to the filament portion on the opposite end from the enlargement through which the retainer wire passes. Additionally, manipulation tabs located on the eyelet and the enlargement render the stabilizer more easily handled during installation.

A second embodiment typically further comprises a knob joined to the enlargement opposite from the filament portion and an eyelet joined to an extension of the opposite end of the filament portion. When the filament is folded about a retainer wire the eyelet may be attached removably to the knob.

The third preferred embodiment includes an elongated filament extension and second enlargement joined to the opposite end of the extension from the first enlargement. The extension is folded about the retainer wire and the enlargement is placed against the opposite side of the teeth.

Although one stabilizer only is typically used in most retainer wire installations, multiple stabilizers may be used easily if desired. Additionally the applicability of the stabilizer is not dependent on any particular positioning along the tooth arch.

These and other objects and features of the present invention will now be described more fully with reference to the following detailed description of the invention and the accompanying drawings.

DESCRIPTION OF THE DRAWINGS

FIG. 1 is a fragmentary plan view showing typical positioning of a stabilizer during installation of a cuspid-to-cuspid retainer wire. FIG. 2 is a cross-sectional view taken along line 2—2 in FIG. 1.

FIG. 3 is a fragmentary plan view showing typical positioning between adjacent teeth during installation of a retainer wire. FIG. 4 is a cross-sectional view taken along line 4—4 in FIG. 3.

FIG. 5 shows a fragmentary plan view showing typical positioning of a stabilizer during installation of a retainer wire. FIG. 6 is a cross-sectional view taken along line 6—6 in FIG. 5.

DETAILED DESCRIPTION OF THE INVENTION

Figure 1:
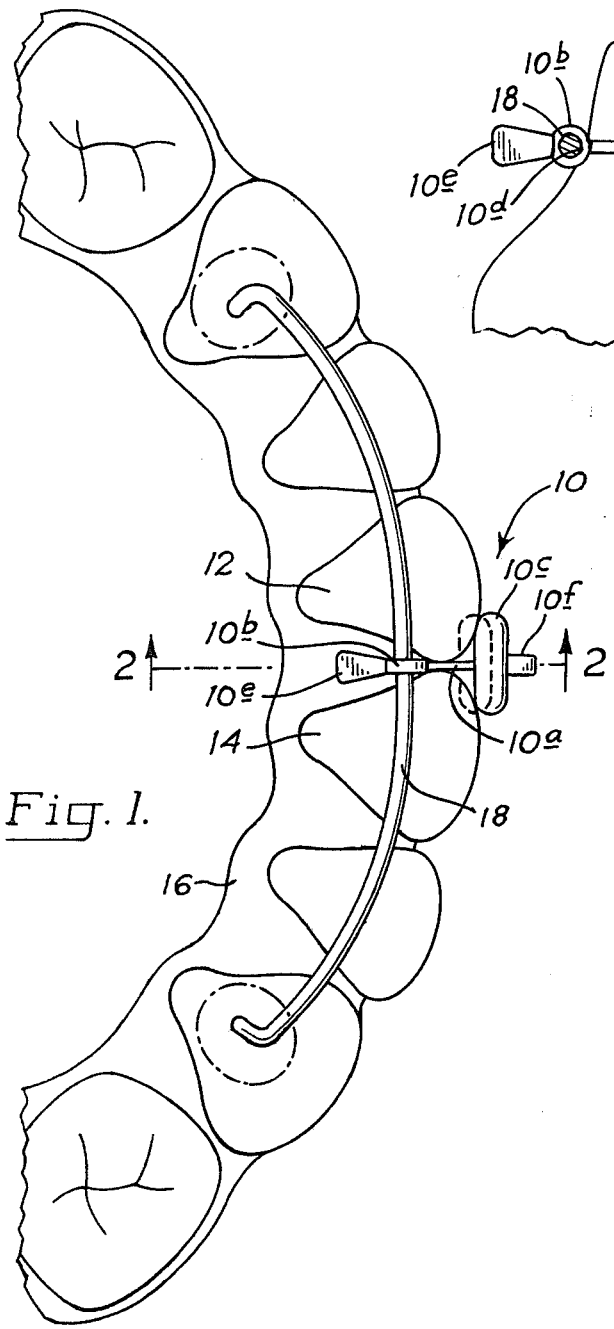
FIGS. 1 and 2 pertain to one embodiment of the invention.
Figure 2:
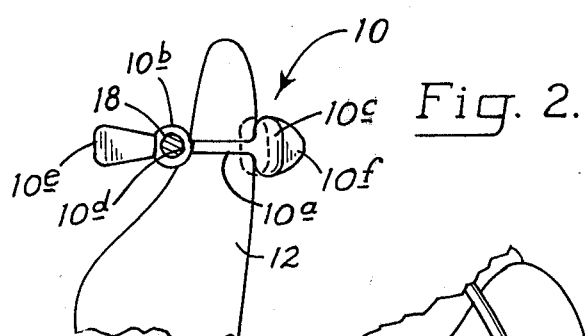

Turning now to FIGS. 1 and 2 in the drawings, one embodiment of a stabilizer which is made in accordance with the invention is shown generally at 10 in operative position between the central incisors 12, 14 of a tooth arch 16 on which a cuspid-to-cuspid retainer wire 18 is being installed.

Stabilizer 10 herein is formed, as by molding, from a thermoset-thermoplastic, polyester-based, isocyanate-terminated, urethane resin which is substantially mouth-acid-resistant. Stabilizer 10 includes an elongated central filament portion 10a which joins at its left end in FIGS. 1 and 2 with an eyelet portion 10b, and at its opposite end with an enlargement 10c. Eyelet 10b extends in a plane which is normal to the plane of FIG. 1 and within the plane of FIG. 2, and includes a central bore 10d. Such portion is also referred to herein as an engaging means. Enlargement 10c is also referred to as a reaction means.

Further included in stabilizer 10 are two manipulation tabs—one of which, 10e, joins as shown with eyelet portion 10b, and the other of which, 10f, joins as shown with enlargement 10c.

As has been mentioned above, in FIGS. 1 and 2 the stabilizer is shown in an operative condition with respect to arch 16 and retainer wire 18. In this condition, bore 10d centrally receives wire 18 as shown, filament portion 10a extends in a stretched condition between teeth 12, 14, and enlargement 10c acts against these teeth on the side opposite from the retainer wire. In dashed lines in FIGS. 1 and 2 what might be thought of as the relaxed-state condition of the stabilizer, prior to its placement for use, is illustrated.

Explaining a typical retainer wire installation procedure utilizing stabilizer 10, and assuming that the wire, as is the case for wire 18, is to be installed substantially symmetrically centrally relative to arch 16, the two teeth to which the opposite ends of the wire are to be bonded are prepared in a conventional fashion to receive the wire ends. The wire is inserted in bore 10d until it has the relative position, vis-a-vis the stabilizer, which is shown in FIG. 2, and the person installing this assemblage, utilizing, if desired, manipulation tabs 10e, 10f, stretches filament portion 10a between teeth 12, 14. If any rotation of the retainer wire is necessary to seat its ends against the "bonding" teeth, this is then performed. The condition which now exists is that the retainer wire is drawn against the inside of the teeth in the arch to which it is adjacent under tension developd in filament portion 10a, which tension is reacted against by engagement of enlargement 10c with the outer sides of teeth 12, 14. A suitable conventional bonding agent is then applied to the wire ends.

No further action by the orthodontist is required to preserve proper positioning of the wire. During the time that the bonding agent is setting up, the stabilizer is left in the condition shown in FIGS. 1 and 2.

When the agent has set, the stabilizer is removed simply by cutting through the eyelet and drawing the stabilizer forwardly between teeth 12, 14.

Figure 3:
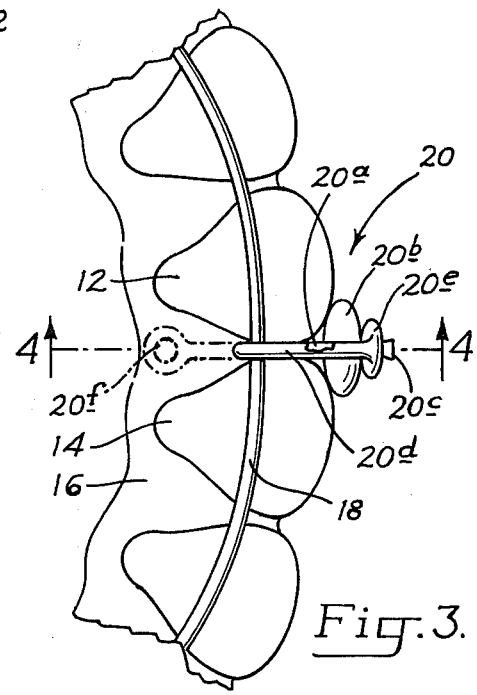
FIGS. 3 and 4 represent another embodiment of the invention.
Figure 4:
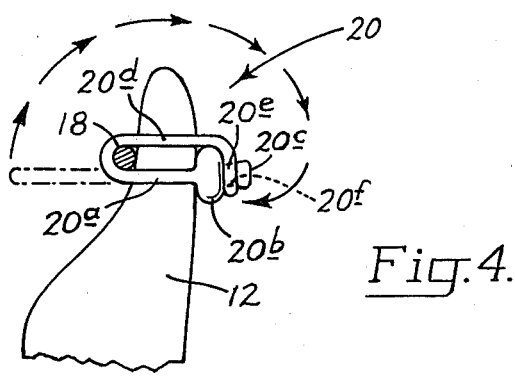

Referring to FIGS. 3 and 4, a second embodiment of a stabilizer made in accordance with the invention is shown generally at 20 in operative position between incisors 12, 14.

Stabilizer 20 herein is formed of the same material used for stabilizer 10. Stabilizer 20 includes an elongated central filament portion 20a which joins at its right end in FIGS. 3 and 4 with an enlargement 20b, also referred to as a reaction means, to which is joined on its opposite side a knob 20c. The left end of filament portion 20a in FIGS. 3 and 4, joins with a filament extension 20d which further joins with an eyelet 20e having a central bore 20f (see FIG. 4). Eyelet 20e extends in a plane substantially normal to the plane of FIGS. 3 and 4. The combination consisting of filament extension 20d and eyelet 20e is also referred to herein as an engaging means.

As can be seen, FIGS. 3 and 4 show stabilizer 20 in an operative condition with respect to arch 16 and retainer wire 18. In this condition filament portion 20a extends in a stretched condition between teeth 12, 14, filament extension 20d folds about the retainer wire and extends in a stretched condition between the same teeth, and eyelet 20e is attached removably to knob 20c. In dashed lines in FIGS. 3 and 4, what might be thought of as the relaxed-state condition of the stabilizer, prior to its placement for use, is illustrated. In this condition, eyelet 20e extends in the same plane as the plane of FIG. 3 and in a plane which is normal to the plane of FIG. 4.

During a retainer wire installation utilizing stabilizer 20, in an installation simiilar to that previously described for stabilizer 10, after the teeth are prepared to receive the wire ends, the stabilizer is installed with the filament portion stretched between teeth 12, 14, and with enlargement 20b on the outside of the teeth, and with eyelet 20e located on the inner side of the teeth. The retainer wire 18 is then placed along the inside of the tooth arch in its desired position. Filament portion 20a is stretched, and filament extension 20d is folded over the wire and extended between teeth 12, 14 with knob 20c inserted into bore 20f. As mentioned earlier, if any rotation of the retainer wire is necessary to seat its ends properly against the "bonding" teeth, this is now done.

The condition which now exists is that the retainer wire is drawn against the inside of the teeth in the arch to which it is adjacent under tension developed both in filament portion 20a, and in filament extension 20d—which tension is reacted against by engagement of eyelet 20e on knob 20c, and by engagement of enlargement 20b with the outer sides of teeth 12, 14.

With the retainer wire now in the proper position, the orthodontist proceeds in the usual manner to apply a bonding agent to secure the wire in place. The stabilizer, remaining in the condition shown in FIGS. 3 and 4, preserves the position of the retainer wire during the time that the bonding agent is setting up.

After the agent has set, the stabilizer is removed simply by cutting through the filament portion, or filament extension, and by drawing the stabilizer forwardly between teeth 12, 14.

Figure 5:
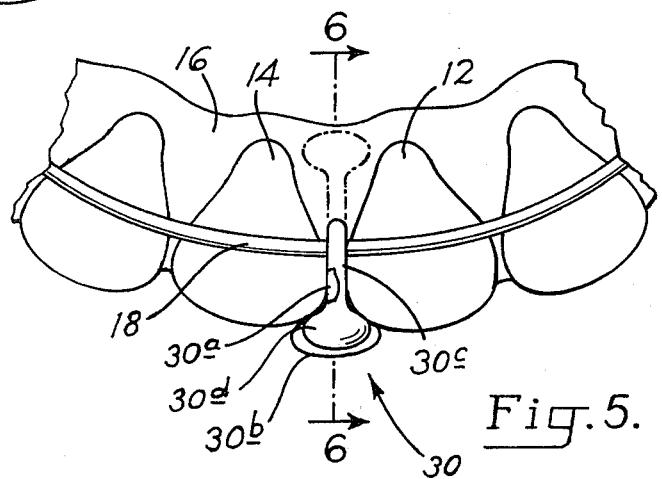
FIGS. 5 and 6 show a third embodiment of the invention.
Figure 6:
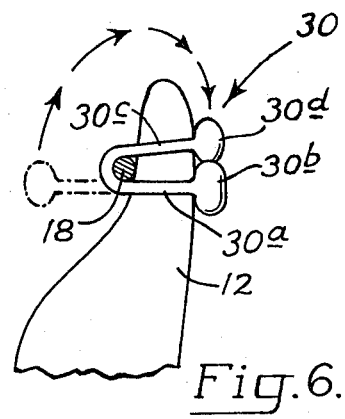

In FIGS. 5 and 6, a third embodiment of the stabilizer which is made in accordance with the invention is shown generally at 30, in operative position between incisors 12, 14.

Stabilizer 30 herein is formed of a plastic resin similar to that used for the first two embodiments. Stabilizer 30 includes an elongated central filament portion 30a which joins at its right end in FIG. 6 (its lower end in FIG. 5) with a first enlargement 30b, also referred to herein as a reaction means, and at its opposite end with a filament extension 30c. Extension 30c joins with a second enlargement 30d. The combination consisting of filament extension 30c and enlargement 30d is also referred to as an engaging means.

In FIGS. 5 and 6, stabilizer 30 is shown in an operative condition with respect to arch 16 and retainer wire 18. In such condition, filament portion 30a extends in a stretched condition between teeth 12, 14, and filament extension 30c folds around the retainer wire and extends coextensively with filament portion 30a between teeth 12, 14. Enlargements 30b and 30d act concurrently against these teeth on the side opposite the retainer wire. The dashed lines in FIGS. 5 and 6 illustrate the relaxed-state condition of the stabilizer prior to its placement for use.

In an installation procedure employing stabilizer 30 in arch 16 with wire 18, the two teeth to which the wire is to be bonded are prepared in the conventional fashion to receive the wire ends and the usual bonding agent. Filament portion 30a is stretched between teeth 12, 14, with enlargement 30b on the outside of the teeth and enlargement 30d on the inside of the teeth. Wire 18 is then placed inside arch 16 in the desired position, and filament extension 30c is folded over the wire and extended coextensively with filament portion 30a between teeth 12, 14 to seat enlargement 30d against the outer side of these teeth as shown. The retainer wire may then be rotated if required in order to set its ends properly against the "bonding" teeth. The retainer wire is thereby held in place, and bonded, in much the same manner as previously described.

When the bonding agent has set, stabilizer 30 is removed by cutting through filament portion 30a or through filament extension 30c, and by drawing the stabilizer forwardly between teeth 12, 14.

Whereas the procedures just described have assumed a central symmetrical positioning for wire 18, and use of but a single stabilizer, it will be appreciated by those skilled in the art that other positionings are possible and desirable in certain instances for such a wire, and in these and other instances, it may be desirable to use more than one stabilizer to assure firm holding of a wire.

While several embodiments of the invention have been described herein, it is appreciated that variations and modifications may be made without departing from its spirit.

It is claimed and desired to secure by Letters Patent:

1. A unitary elasticized stabilizer for immobilizing temporarily a tooth-to-tooth retainer wire or the like during its installation, said stabilizer comprising
   an elongated filament portion sized to fit and extend between a pair of adjacent teeth,
   an eyelet formed adjacent one end of said filament portion for receiving and engaging such a wire and, through stretching of the filament portion, for urging the wire toward one side of such teeth, and
   reaction means joined adjacent the other end of said filament portion for acting against the opposite side of such teeth to inhibit withdrawal of the filament portion in a direction toward the one side of the teeth.

2. A unitary elasticized stabilizer for immobilizing temporarily a tooth-to-tooth retainer wire or the like during its installation, said stabilizer, in operative condition engaging and immobilizing such a wire, comprising
   an elongated filament portion fitting and extending between a pair of adjacent teeth in a stretched condition,
   an eyelet formed adjacent one end of said filament portion receiving and engaging such a wire and urging it toward one side of such teeth, and
   reaction means joined adjacent the other end of said filament portion acting against the opposite side of such teeth inhibiting withdrawal of the filament portion in a direction toward the one side of the teeth.

3. A unitary elasticized stabilizer for immobilizing temporarily a tooth-to-tooth retainer wire or the like during its installation, said stabilizer comprising
   an elongated filament portion sized to fit and extend between a pair of adjacent teeth,
   means joined adjacent one end of said filament portion for engaging such a wire and, through stretching of the filament portion, for urging the wire toward one side of such teeth,
   reaction means joined adjacent the other end of said filament portion for acting against the opposite side of such teeth to inhibit withdrawal of the filament portion in a direction toward the one side tooth, and
   a pair of manipulation tabs, with one projecting from said engaging means, and the other projecting from said reaction means.

4. A unitary elasticized stabilizer for immobilizing temporarily a tooth-to-tooth retainer wire or the like during its installation, said stabilizer, in operative condition engaging and immobilizing such a wire, comprising
   an elongated filament portion fitting and extending between a pair of adjacent teeth in a stretched condition,
   means joined adjacent one end of said filament portion engaging such a wire and urging it toward one side of such teeth,
   reaction means joined adjacent the other end of said filament portion acting against the opposite side of such teeth inhibiting withdrawal of the filament portion in a direction toward the one side of the teeth, and
   a pair of manipulation tabs, with one projecting from said engaging means, and the other projecting from said reaction means.

5. A unitary elasticized stabilizer for immobilizing temporarily a tooth-to-tooth retainer wire or the like during its installation, said stabilizer comprising
   an elongated filament portion sized to fit and extend between a pair of adjacent teeth,
   means joined adjacent one end of said filament portion for engaging such a wire, and, through stretching of the filament portion, for urging the wire toward one side of such teeth,
   reaction means joined adjacent the other end of said filament portion for acting against the opposite side of such teeth to inhibit withdrawal of the filament portion in a direction toward the one side of the teeth, and
   a knob joined to said reaction means opposite said filament portion,
   said engaging means including an elongated filament extension joined to said filament portion which is foldable about such a retainer wire, and an eyelet joined to said extension which is removably attachable to said knob.

6. A unitary elasticized stabilizer for immobilizing temporarily a tooth-to-tooth retainer wire or the like during its installation, said stabilizer comprising
   an elongated filament portion sized to fit and extend between a pair of adjacent teeth,
   means joined adjacent one end of said filament portion for engaging such a wire and, through stretching of the filament portion, for urging the wire toward one side of said teeth, and
   reaction means joined adjacent the other end of said filament portion for acting against the opposite side of said teeth to inhibit withdrawal of the filament portion in a direction toward the one side of the teeth,
   said engaging means including an elongated filament extension joined at one end to said filament portion foldable about such a retainer wire, and an enlargement joined with the opposite end of said extension actable against the opposite side of such teeth.

7. A unitary elasticized stabilizer for immobilizing temporarily a tooth-to-tooth retainer wire or the like during its installation, said stabilizer, in operative condition engaging and immobilizing such a wire, comprising
   an elongated filament portion fitting and extending between a pair of adjacent teeth in a stretched condition,
   means joined adjacent one end of said filament portion engaging such a wire and urging it toward one side of such teeth,
   reaction means joined adjacent the other end of said filament portion acting against the opposite side of such teeth inhibiting withdrawal of the filament portion in a direction toward the one side of the teeth, and
   a knob joined to said reaction means opposite said filament portion,
   said engaging means including an elongated filament extension joined to said filament portion and folded about the wire, and an eyelet joined to said extension removably attached to said knob.

8. A unitary elasticized stabilizer for immobilizing temporarily a tooth-to-tooth retainer wire or the like during its installation, said stabilizer, in operative condition engaging and immobilizing such a wire, comprising an elongated filament portion fitting and extending between a pair of adjacent teeth in a stretched condition, means joined adjacent one end of said filament portion engaging such a wire and urging it toward one side of such teeth, and reaction means joined adjacent the other end of said filament portion acting against the opposite side of such teeth inhibiting withdrawal of the filament portion in a direction toward the one side of the teeth, said engaging means including an elongated filament extension joined at one end of said filament portion and folded about the wire, and an enlargement joined to the opposite side of said extension acting against the opposite side of such teeth.

* * * * *